US009345755B2

(12) United States Patent
Slingluff, Jr. et al.

(10) Patent No.: US 9,345,755 B2
(45) Date of Patent: May 24, 2016

(54) COMPOSITION AND METHODS FOR TREATING MELANOMA

(71) Applicants: Craig L. Slingluff, Jr., Charlottesville, VA (US); Victor H. Engelhard, Crozet, VA (US)

(72) Inventors: Craig L. Slingluff, Jr., Charlottesville, VA (US); Victor H. Engelhard, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/379,100

(22) PCT Filed: Feb. 20, 2013

(86) PCT No.: PCT/US2013/026853

§ 371 (c)(1),
(2) Date: Aug. 15, 2014

(87) PCT Pub. No.: WO2013/126402

PCT Pub. Date: Aug. 29, 2013

(65) Prior Publication Data

US 2015/0231217 A1 Aug. 20, 2015

Related U.S. Application Data

(60) Provisional application No. 61/600,928, filed on Feb. 20, 2012.

(51) Int. Cl.
*A61K 38/00* (2006.01)
*A61K 39/00* (2006.01)

(52) U.S. Cl.
CPC ....... *A61K 39/0011* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 6,558,951 B1 | 5/2003 | Tomai et al. | |
| 7,763,259 B2 | 7/2010 | Garcea et al. | |
| 7,820,786 B2* | 10/2010 | Thomson | C07K 14/005 424/184.1 |
| 8,586,006 B2* | 11/2013 | Hood | 424/1.11 |
| 8,815,249 B2* | 8/2014 | Humphreys | A61K 39/385 424/185.1 |
| 2004/0077548 A1* | 4/2004 | Cerundolo | C07K 14/4748 424/192.1 |
| 2007/0099251 A1* | 5/2007 | Zhang | G01N 33/574 435/7.23 |
| 2008/0119636 A1 | 5/2008 | Celis | |
| 2009/0081248 A1* | 3/2009 | Paterson | A61K 39/0011 424/192.1 |
| 2010/0291145 A1* | 11/2010 | Humphreys | A61K 39/385 424/208.1 |
| 2012/0231030 A1* | 9/2012 | Derouazi | A61K 39/0005 424/192.1 |
| 2013/0259826 A1* | 10/2013 | Lenz | A61K 39/39 424/85.2 |

FOREIGN PATENT DOCUMENTS

| | | | |
|---|---|---|---|
| WO | 2005053738 | * | 6/2005 |
| WO | 2008021290 | * | 2/2008 |

OTHER PUBLICATIONS

Slingluff et al., Clin. Cancer Res. 2007; 13(21):6386-95.*
Ezzell (J. NIH Res. 1995 7:46).*
Spitler (Cancer Biotherapy, 1995, 10:1-3).*
Boon (Adv. Can. Res. 1992 58:177-210).*
Haigh et al, Oncology vol. 13 p. 1561 (1999.*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987.*
Lin et al Biochemistry USA vol. 14:1559-1563 (1975).*
Chianese-Bullock, et al., "MAGE-A1-, MAGE-A10-, and gp100-Derived Peptides Are Immunogenic When Combined with Granulocyte-Macrophage Colony-Stimulating Factor and Montanide ISA-51 Adjuvant and Administered as Part of a Multipeptide Vaccine for Melanoma", Journal of Immunology, vol. 74, No. 5, 3080-3086 (2005).
Slingluff, C., et al., "Immunologic and Clinical Outcomes of a Randomized Phase II Trial of Two Multipeptide Vaccines for Melanoma in the Adjuvant Setting", Clinical Cancer Research, vol. 13, No. 21, 6386-6395 (2007).
Rogel, A., et al., "A long peptide from MELOE-1 contains multiple HLA class II T cell epitopes in addition to the HLA-A*0201 epitope: an attractive candidate for melanoma vaccinations", Cancer Immunol. Immunotherapy, vol. 60, No. 3, 327-337 (2011).
Bijker, M., et al., "CD8+ CTL Priming by Exact Peptide Epitopes in Incomplete Freund's Adjuvant Induces a Vanishing CTL Response, whereas Long Peptides Induce Sustained CTL Reactivity1", Journal of Immunology, vol. 179, No. 8, 5033-5040 (2007).
Van Der Burg, S., et al., "Improved peptide vaccine strategies, creating synthetic artificial infections to maximize immune efficacy", Advanced Drug Delivery Reviews, vol. 58, No. 8, 916-930 (2006).
Slingluff, C., et al., "Randomized Multicenter Trial of the Effects of Melanoma-Associated Helper Peptides and cyclophosphamide on the Immunogenicity of a Multipeptide Melanoma Vaccine", Journal of Clinical Oncology, Jun. 2011, 1-9.
Kittlesen, D., et al., "Human Melanoma Patients Recognize an HLA-A1-Restricted CTL Epitope from Tyrosinase Containing Two Cysteine Residues" Implications for Tumor Vaccine Development, Journal of Immunology 1998; 160: 2099-2106.
Sabbatini, P., et al., "Phase I Trial of Overlapping Long Peptides from a Tumor Self-Antigen and Poly-ICLC Shows Rapid Induction of Integrated Immune Response in Ovarian Cancer Patients", Clinical Cancer Research 2012;18:6497-6508.

* cited by examiner

*Primary Examiner* — Sheela J Huff
(74) *Attorney, Agent, or Firm* — Rodney L. Sparks

(57) ABSTRACT

The present invention encompasses novel peptides useful for preventing and treating cancer, particularly melanoma. Multiple sequences of interest are provided and these sequences have been incorporated into other peptides to obtain a series of peptides of about 30 amino acid residues in length wherein the properties of each combine to yield an effective cocktail for treating melanoma, which surpasses the use of single peptides as immunogens, as well as shorter peptides as immunogens.

12 Claims, 2 Drawing Sheets

COMPOSITION AND METHODS FOR TREATING MELANOMA

CROSS REFERENCE TO RELATED APPLICATIONS

This application is a national stage filing of International Application No. PCT/US2013/026853, filed Feb. 20, 2013, which is entitled to priority pursuant to 35 U.S.C. §119(e) to U.S. provisional patent application No. 61/600,928, filed on Feb. 20, 2012. The entire disclosure of the afore-mentioned patent applications are incorporated herein by reference.

STATEMENT REGARDING FEDERALLY SPONSORED RESEARCH OR DEVELOPMENT

This invention was made with government support under CA057653 and CA134060 awarded by the National Institute of Health. The government has certain rights in the invention.

BACKGROUND

The most effective and durable therapies for advanced melanoma are immune therapies, both FDA-approved (Interleukin-2 (IL-2); CTLA-4 antibody), and in development (e.g., antibody blockade of PD-1/PD-L1). Each of these induces durable clinical benefit in patient subsets; however, overall clinical response rates remain no higher than 20% for IL-2 and for CTLA-4 antibody, and about 30% in early trials with PD-1 antibody. These therapies are mediated directly or indirectly through T cell activation; thus, they are proof-of-principle for the ability of T cell-directed therapies to control melanoma. T cells act by receptor-mediated recognition of specific peptide antigens in association with MHC molecules. Antitumor T cells arise spontaneously in melanoma patients and likely have a role in immune surveillance and immuno-editing, and their presence within tumors is associated with improved survival. However, tumor-infiltrating T cells are typically rendered dysfunctional in the tumor micro-environment by numerous soluble and cell-associated factors, including PD-1/PD-L1. Immunologic control of metastatic melanoma can be obtained by therapy that reverses tumor-associated immune dysfunction. However, current mono-therapies are associated with significant toxicity, and each benefits only a minority of patients.

Cancer vaccines can expand T cells that specifically lyse human melanoma cells. As monotherapy, peptide vaccines induce clinical responses in only 3-5% of melanoma patients, but they can induce durable clinical responses in some patients. Importantly, they may synergize with other immune therapies to improve clinical benefit when administered as part of combination immunotherapy. For example, clinical outcome of IL-2 therapy was improved significantly by co-administration with a melanoma peptide vaccine. The vaccine used in that regimen incorporated only one short peptide (IMDQVPFSV, $gp100_{209-2M}$), restricted by HLA-A2, and it was administered in incomplete Freund's adjuvant (IFA). IFA is not optimal for inducing Th1/Tc1 T cell responses, and it may negatively impact T cell persistence and homing to tumor, especially when administered with short peptides. Optimization of peptide vaccines is likely to increase the therapeutic effect of this and other combination therapies. Also, with recent FDA approval of a defined antigen vaccine for prostate cancer, there is support for continued optimization of cancer vaccines. Current melanoma vaccines are not optimized: both the antigens and the adjuvants may be improved. Short peptides can be presented by non-professional antigen-presenting cells (APC) at the vaccine site and may contribute to tolerance or anergy. However, long (30-mer) peptides require processing by dendritic cells and are presented only by professional APC. They offer substantial promise as improved antigens. A long peptide vaccine against HPV has induced dramatic regressions of vulvar neoplasia.

Long Peptides:

Short peptides may bind directly to MHC molecules on cells that are not professional antigen-presenting cells (APC), thereby potentially inducing tolerance or anergy. Instead, long peptides have a tertiary structure that protects from exopeptidase-mediated degradation, and long peptides must be internalized by professional APC and processed for presentation (e.g. $CD11c^+$ DC). Recent work with long (30-mer) peptides that encompass short minimal epitopes suggests that these longer peptides may be more effective immunogens than the minimal peptides. The extra length contributes to a tertiary structure that may protect from peptidases, and they are too long to be presented directly on MHC; so processing is required. This further ensures that the peptides are presented just by professional antigen-presenting cells (APC). A vaccine using long peptides for squamous vulvar neoplasia has induced high rates of clinical regressions, supporting clinical activity of long peptide vaccines. Vaccination with 4 long peptides from NY-ESO-1 in ovarian cancer has demonstrated safety in humans and has demonstrated immunogenicity, including the ability to induce $CD8^+$, $CD4^+$, and antibody responses to the peptide NY-ESO-$1_{79-108}$ (Sabbatini et al., 2012, Clin. Cancer Res. 18:6497). Unlike short peptides, long peptides induce memory $CD8^+$ T cell responses that are boosted dramatically on repeat vaccination in mice, and induce substantially improved tumor control than vaccination with short peptides. Induction of helper T cells reactive to epitopes within the long peptide have been implicated as necessary for long-term T cell memory. Using the long peptides in LPV7 as a vaccine promises to induce a broad and more durable adaptive immune responses against multiple antigens.

CD4 T Cell Induction, to Activation of CD40:

The effects of adjuvants are supported by concurrent stimulation of CD40, which is most naturally effected by expression of CD40L on activated CD4 T cells at the site of vaccination and in draining nodes. An effective way to ligate CD40 specifically on dendritic cells (DC) in the vaccine-site microenvironment (VSME) and in vaccine-draining lymph nodes (VDLN) is to take advantage of physiologic systems where activation of $CD4^+$ cells in the VSME and VDLN will upregulate CD40L on those cells. $CD40L^+$ CD4 cells in turn license professional APC (DC) in tissues where antigen is presented. The peptides in the LPV7 mixture contain immunogenic epitopes for $CD4^+$ T cells. This strategy can be expected to induce CD40L expression and CD40 activation, which can then synergize with activation of TLR.

Human Experience with Long Peptides in Cancer Vaccines:

A human clinical study of vaccination with 4 long peptides from NY-ESO-1 (residues 79-108, 100-129, 121-150, 142-173), has been performed by Dr. Sacha Gnjatic in 21 patients with high-risk ovarian cancer patients (Sabbatini et al., 2012, Clin. Cancer Res. 18:6497). NY-ESO-1 is a cancer-testis antigen. Vaccines were administered subcutaneously (SQ) every 3 weeks alone (n=3), combined with Montanide ISA-51 (IFA, n=9), or combined with IFA+poly-ICLC (n=9). The vaccines were well tolerated. For peptides+IFA, injection site reactions were frequent but self-limited (grade I-II); systemic effects included grade I fatigue and headache. The addition of poly-ICLC led to more intense injection site reactions in some patients. Two grade 3 toxicities were recorded: pneumonia not related to vaccine, and neutropenia possibly related. The long peptides induced all three arms of the adaptive immune response. PolyICLC improved induction and magnitude of antibody (Ab) responses, including responses to multiple epitopes within peptide NY-ESO-1$_{79-108}$, in most patients. CD4 T cells were consistently induced in the large majority of patients vaccinated with IFA or IFA+Poly-ICLC. CD8 T cell responses were observed in most patients, with greater consistency, magnitude, and breadth when poly-ICLC was added. T cell responses were typically polyfunctional and polyclonal, with responses to multiple epitopes within NY-ESO-1$_{79-108}$. Multiple T cell epitopes have been defined within the NY-ESO-1$_{79-108}$ sequence (Table 1). Responses were observed to many of the defined antigens contained in this sequence, as well as to others, in the context of rarer HLA class I and class II alleles.

There is a long felt need in the art for compositions and methods useful for treating and preventing cancer. The present invention satisfies these needs.

SUMMARY OF THE INVENTION

The present application discloses a series of peptides found to have immunogenic activity that can be used singly or in combination to elicit an immunogenic response and are useful for preventing and treating cancer. The present invention is based on the discovery and use disclosed herein of a cocktail comprising more than one immunogenic long peptide to better treat and prevent cancer than using just one immunogenic peptide, particularly short peptides. More specifically, the present application discloses compositions and methods for using longer peptides than have been routinely used in the past, as well as the use of combinations of more than one long peptide. The present application further discloses vaccine compositions comprising immunogenic peptides of about 30 amino acids in length. The peptides are referred to as long peptides and the compositions comprising these long peptides are referred to as Long Peptide Vaccines ("LPV") herein. The present application further discloses that a long peptide of the invention elicits a much stronger immunogenic response than its short counterpart.

In one embodiment, the present invention provides a set of peptides, approximately 30 amino acids in length, to be used together as a cocktail or individually as a component of a vaccine (immunogen) to prevent or to treat human malignant melanoma and other cancers. When administered, the cocktail or combination of peptides elicits an immunogenic response.

These peptides are derived directly from the naturally-occurring sequences of proteins expressed in human melanomas and other cancers. Those proteins include, for example, gp100, tyrosinase, MAGE-A1, and MAGE-A10. The long peptides of the invention all include specific shorter sequences within them, where those shorter sequences represent the minimal epitopes recognized by human T lymphocytes (T cells) that can recognize and kill human cancer cells expressing those proteins, in conjunction with appropriate Class I MHC molecules. In one aspect, the inserted shorter sequences are about 8 to about 12 amino acid residues in length.

The long peptides of the invention were selected from many thousands that could have been chosen, by their inclusion of defined short epitopes for human T cells, by low numbers of cysteine residues, by solubility, and by their ability to reconstitute T cell epitopes in vitro. Therefore, the present invention provides for the use of a cocktail of peptides useful for treatment, wherein the peptides have multiple desirable properties for preventing and treating melanoma. Although the invention encompasses using multiple peptides, when the peptides are administered they do not necessarily need to be administered in the same cocktail or composition.

The present invention further includes the use of adjuvants and additional therapeutic agents as part of the peptide treatment. For example, an additional therapeutic agent can include one of the other immunomodulating agents discussed herein, a chemotherapeutic agent, or an antimicrobial agent such as an antimicrobial or an antiviral. The construction of the longer peptides comprising the short peptides of interest and the specific peptides used are based on a series of desired characteristics and properties as disclosed herein. For example, the added length of these peptides protects them from proteolytic degradation in vivo, and ensures that the relevant short peptide epitopes within them are presented only by professional antigen-presenting cells. This is an advance over the prior art use of the shorter peptides because the shorter peptides can induce tolerance, and experimental evidence shows that longer peptides can, instead, induce strong and durable immune responses. Long peptides were selected to take into account multiple features: avoidance of N-terminal glutamine and glutamic acid residues, minimizing cysteine residues, and maximizing polar residues to improve solubility in aqueous solutions.

The long peptides of the invention (SEQ ID NOs:1-8) incorporate well-characterized minimal epitopes restricted by a wide range of HLA alleles (LPV). In one embodiment, the peptide cocktails (combinations), may be administered with adjuvants stimulating toll-like receptors (TLR), to take advantage of the innate immune system response to viral and other exogenous pathogens, with or without a depot (e.g., incomplete Freund's adjuvant, IFA) at the vaccine site.

The long peptides of the invention can also be used in combination with other immunogenic peptides. The long peptides of the invention comprise those peptides having the amino acid sequences of SEQ ID NOs:1-8, and immunogenically active fragments and homologs thereof. Other useful peptides with shorter sequences include, but are not limited to, those peptides having the amino acid sequences of SEQ ID NOs:9-21, and immunogenically active fragments and homologs thereof.

The use of each of the long peptides of the invention (SEQ ID NOs:1-8) as disclosed and taught herein is a novel use for these peptides. Furthermore, they have not been disclosed, taught, or contemplated as such before. Additionally, their various combinations as a cocktail for use in humans is disclosed herein for the first time. These peptides are soluble in aqueous solutions and thus can be used, for example, as an injected or topically applied vaccine.

Provided below are some peptides of the invention:

SEQ ID NO: 1
FTIPYWDWRDAEKSDICTDEYMGGQHPTNP (also referred to as peptide #1)

SEQ ID NO: 2
SKASSSLQLVFGIELMEVDPIGHLYIFAT (also referred to as peptide #2C)

SEQ ID NO: 3
SMHNALHIYMDGTMSQVQGSANDPIFLLHH (also referred to as peptide #3)

SEQ ID NO: 4
VPLAHSSSAFTIMDQVPFSVSVSQLRALDG (also referred to as peptide #4)

SEQ ID NO: 5
VIWEALNMMGLYDGMEHLIYGEPRKLLTQD (also referred to as peptide #5)

SEQ ID NO: 6
LLHLAVIGALLAVGATKVPRNQDWLGVSRQL (also referred to as peptide #6)

SEQ ID NO: 7
SREEEGPSTSCILESLFRAVITKKVADLVG (also referred to as peptide #7B)

SEQ ID NO: 8
FTIPYWDWRDAEKSDICTDEYMGGQHPTN (also referred to as peptide #8)

SEQ ID NO: 9
DAEKSDICTDEY

SEQ ID NO: 10
EVDPIGHLY

SEQ ID NO: 11
YMDGTMSQV

SEQ ID NO: 12
IMDQVPFSV

SEQ ID NO: 13
GLYDGMEHL

SEQ ID NO: 14
ALLAVGATK

SEQ ID NO: 15
SLFRAVITK

SEQ ID NO: 16
MPFATPMEA

SEQ ID NO: 17
LAMPFATPM

SEQ ID NO: 18
ARGRESRLL

SEQ ID NO: 19
EFYLAMPFATPM

SEQ ID NO: 20
PFATPMEAERARR

SEQ ID NO: 21
LLEFYLAMPFATPM

Cysteine residues found in the peptides above are highlighted in bold face. SEQ ID NOs:1-8 and their use are the long peptides disclosed herein. SEQ ID NOs: 1 and 8 differ by one amino acid at the C terminus. SEQ ID NOs: 9-15 are the short peptides comprising the epitope of interest for SEQ ID NOs:1-8. SEQ ID NOs:16-21 are short peptides representing previously defined epitopes in NY-ESO-1$_{79-108}$ (see Table 1).

In one embodiment, the present invention provides an immunogenic vaccine composition for use in treating and preventing cancer. In one aspect, the composition comprises at least one isolated peptide selected from the group having SEQ ID NOs:1-8, or biologically active fragments or homologs thereof. The vaccine composition can also include an adjuvant or a pharmaceutically acceptable carrier. In one aspect, at least two peptides are included in the composition. Any combination of the peptides can be used. In one aspect, the immunogenic vaccine comprises six isolated peptides. In another aspect, it includes seven isolated peptides. In one aspect, when six peptides are used, the six peptides have SEQ ID NOs:3-8. In one aspect, when the composition comprises seven peptides the seven peptides have SEQ ID NOs:2-8.

In one embodiment, a vaccine composition comprising at least one long peptide having SEQ ID NOs:1-8, further comprises at least one peptide selected from the group having SEQ ID NOs:9-21.

The compositions can be prepared according to the dose needed or can be administered based on the dose needed. In one embodiment, the amount of each peptide per dose is from about 10 μg to about 10,000 μg. In some cases, up to about 2,000 μg can be used. In another embodiment, the amount of each peptide per dose is from about 100 μg to about 1,000 μg. In one embodiment, the amount of each peptide per dose is 300 μg. The amount of each peptide used when multiple peptides are administered does not have to be the same.

In one embodiment, an immunogenic fragment or homolog of a peptide of the invention is used. In one aspect, the biologically active fragments or homologs of the peptide share at least about 50% sequence identity with the peptide. In another aspect, they share at least about 75% sequence identity with the peptide. In yet another aspect, they share at least about 95% sequence identity with the peptide.

In one embodiment, at least one of the active fragments or homologs being used comprises a serine or alanine amino acid substitution for a cysteine residue. In another embodiment, at least one of the active fragments or homologs being used comprises at least one conservative amino acid substitution. The present invention encompasses the use of amino acid substitutions at any of the positions, as long as the resulting peptide maintains the desired biologic activity of being immunogenic. The present invention further includes the peptides where amino acids have been deleted or inserted, as long as the resulting peptide maintains the desired biologic activity of being immunogenic.

The present invention further provides compositions and methods useful for eliciting an immunogenic response and for preventing and treating cancer. In one embodiment, the method comprises administering to a subject a vaccine composition comprising at least one isolated peptide selected from the group having SEQ ID NOs:1-8, or biologically active fragments and homologs thereof, optionally an adjuvant, and optionally a pharmaceutically acceptable carrier. In one aspect, the composition comprises two, three, four, five, six, seven, or eight of the different peptides. When the composition comprises six peptides, in one aspect, the peptides have SEQ ID NOs:3-8. In one aspect, when seven peptides are used the peptides have SEQ ID NOs:2-8. In one aspect, the composition further comprises at least one peptide selected from the group having SEQ ID NOs:9-21.

In one embodiment, the method provides for administering a composition wherein the amount of each peptide per dose is from about 10 μg to about 10,000 μg. In another embodiment, the amount of each peptide per dose is from about 100 μg to about 1,000 μg. In one embodiment, the amount of each peptide per dose is 300 μg.

In one embodiment, the methods of the invention provide for administering the vaccine composition to a subject at least about 2 times to about 50 times. In one embodiment, the method comprises administering the vaccine composition to a subject at least about 5 times to about 30 times. In one embodiment, the methods of the invention provide for administering the vaccine composition to a subject at least about 10 times to about 20 times. The method also provides for administering the composition daily, or weekly, or monthly. One of ordinary skill in the art can design a regimen based on the needs of a subject, taking into account the age, sex, and health of the subject.

The methods of the present invention are useful for preventing and treating cancer. Cancers encompassed by the compositions and methods of the invention include, but are not limited to, melanoma, lung cancer, MMMT, bladder cancer, ovarian cancer, uterine cancer, endometrial cancer, breast cancer, head and neck cancer, liver cancer, pancreatic cancer, esophageal cancer, stomach cancer, cervical cancer, prostate cancer, adrenal cancer, lymphoma, leukemia, salivary gland cancer, bone cancer, brain cancer, cerebellar cancer, colon cancer, rectal cancer, colorectal cancer, oronasopharyngeal cancer, NPC, kidney cancer, skin cancer, basal cell carcinoma, hard palate carcinoma, squamous cell carcinoma of the tongue, meningioma, pleomorphic adenoma, astrocytoma, chondrosarcoma, cortical adenoma, hepatocellular carcinoma, pancreatic cancer, squamous cell carcinoma, and adenocarcinoma. The combination of peptides used can be varied based on what is known about the cancer, etc.

As described herein, the peptides are immunogenic, so a useful composition comprising one or more of the long peptides of the invention, even when using active fragments or homologs, or additionally short peptides, elicits an immunogenic response.

One of ordinary skill in the art will appreciate the strategy provided herein to use different peptides with different epitopes to broaden the response and ensure better results, as well as the rationale for using the long peptides. In one embodiment, short peptides can be added to the composition.

The long peptides having SEQ ID NOs:1-8, or effective homologs or fragment thereof, when used together as a cocktail of two or more peptides represent a combination or cocktail of peptides as disclosed herein and referred to as a Long Peptide Vaccine (LPV). In particular, when the peptides used have SEQ ID NOs:2-8, the combination will be referred to as LVP7. When SEQ ID NOs:3-8 are used, that set of six peptides is also referred to as LPV6.

In one aspect, a homolog of a peptide of the invention is one with one or more amino acid substitutions, deletions, or additions, and with the sequence identities described herein. In one aspect, the substitution, deletion, or addition is conservative. In one aspect, a serine or an alanine is substituted for a cysteine residue in a peptide of the invention.

In one embodiment, the subject is a mammal. In another embodiment, the mammal is a human.

The present invention encompasses the use of purified isolated, recombinant, and synthetic peptides.

The present invention further provides methods for solubilizing peptides which are not easily soluble in an aqueous solution. The method encompasses peptides comprising about 8 amino acid residues to about 35 amino residues. The method comprises adding a known amount of a peptide to an aqueous solution, adjusting the pH of the solution within a range of about 4 to about 12 until the peptide solubilizes. Furthermore, the method encompasses solubilization wherein the peptide is not degraded or hydrolyzed once solubilized. Methods are described herein and are known in the art for testing a peptide to ensure that it has not been hydrolyzed or degraded. In one aspect, the peptide is selected from the group of peptides having SEQ ID NOs:1-21, or biologically active fragments or homologs thereof. In one aspect, the amount of peptide ranges from about 0.1 mg/ml to about 100 mg/ml in aqueous solution. In one aspect, more than one peptide is added to the solution.

The present invention further encompasses a method for preparing a sterile composition comprising at least one peptide having about 8 amino acid residues to about 35 amino residues. The method comprises adding a known amount of at least one peptide to an aqueous solution, adjusting the pH of the solution within a range of about 4 to about 12 until the peptide solubilizes, further wherein the peptide is not degraded or hydrolyzed once solubilized. Then the solution is subjected to sterile-filtering, and can then be aliquoted and vialed. In one aspect, the invention encompasses optionally mixing the solution of at least one peptide with one or more solutions comprising at least one different peptide, and vialing the mixture to an amount ranging from about 1.0 µg/vial to about 10,000 µg/vial. In one aspect, the vial contains a volume of about 0.5 to about 1.0 ml. In one aspect at least one of the peptides is selected from the group having SEQ ID NOs:1-21, or biologically active fragments or homologs thereof.

The invention further provides kits comprising peptides and cocktails of the invention useful for eliciting an immunogenic response, and further includes an applicator and an instructional material for the use thereof.

Various aspects and embodiments of the invention are described in further detail below.

DETAILED DESCRIPTION

Abbreviations and Acronyms

Figure 1:
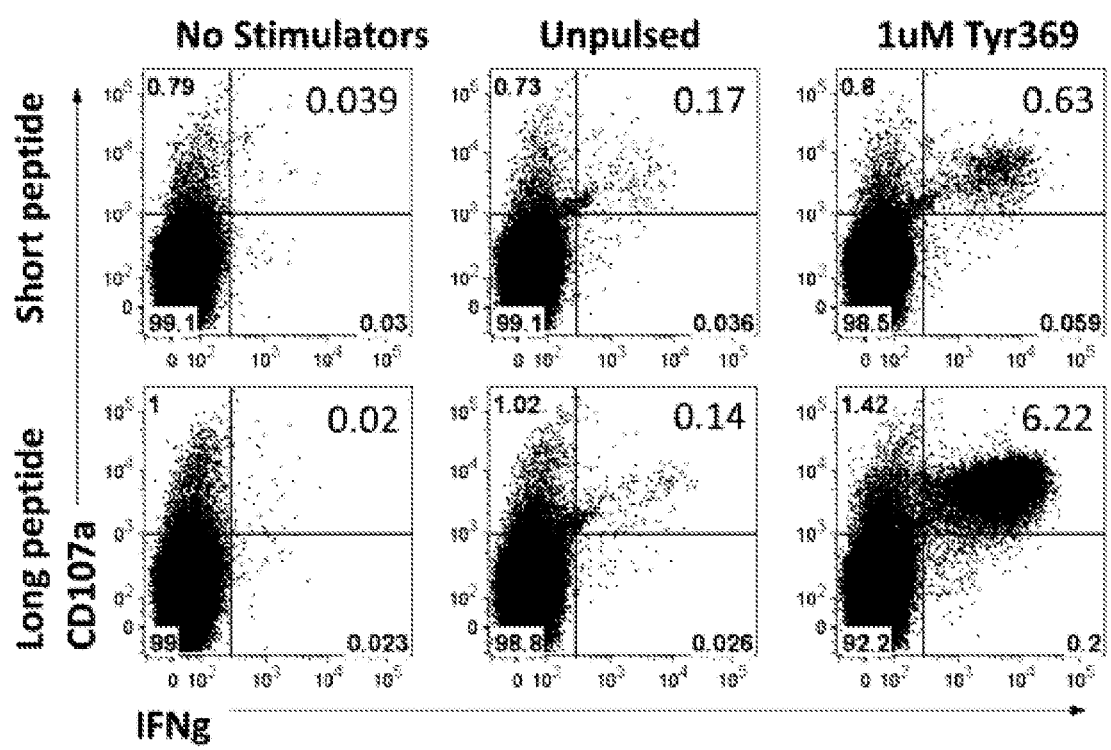
FIG. 1. Albino HLA-A2 Tg mice were immunized with 100 µg of the short or long tyrosinase peptide (SEQ ID NOs: 11 and 3, respectively), 50 µg FGK45 (anti-CD40) and 100 µg of CpG i.v. Mice were revaccinated 6 days later. CD8 T cells were enriched from the spleens and lymph nodes 5 d after the 2nd immunization, and the T cell response was evaluated by measuring IFNg production and CD107a expression in an ex vivo assay.

12MP—12 melanoma peptides
APC—antigen-presenting cells
CTA—cancer-testis antigens
DC—dendritic cells
IFA—incomplete Freund's adjuvant
LPV—long peptide vaccine (a vaccine or cocktail comprising long peptides as defined herein)
LPV6—a vaccine cocktail of six long peptides (typically SEQ ID NOs:3-8)
LPV7—a vaccine of seven long peptides (typically SEQ ID NOs:2-8)
LR—Lactated Ringer's
TLR—toll-like receptors
MDP—melanocytic differentiation proteins UVA HITC—University of Virginia Human Immune Therapy Center VSME—vaccine-site microenvironment VDLN—vaccine-draining lymph nodes

DEFINITIONS

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

A disease or disorder is "alleviated" if the severity of a symptom of the disease, condition, or disorder, or the frequency with which such a symptom is experienced by a subject, or both, are reduced.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, an "analog" of a chemical compound is a compound that, by way of example, resembles another in structure but is not necessarily an isomer (e.g., 5-fluorouracil is an analog of thymine).

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

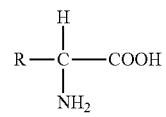

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

The term "aqueous solution" as used herein can include other ingredients commonly used, such as sodium bicarbonate described herein, and further includes any acid or base solution used to adjust the pH of the aqueous solution while solubilizing a peptide.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the peptides encompasses natural or synthetic portions of a longer peptide or protein that are capable of specific binding to their natural ligand or of performing the desired function of the protein, for example, a fragment of a protein of larger peptide which still contains the epitope of interest and is immunogenic.

The term "biological sample," as used herein, refers to samples obtained from a subject, including, but not limited to, skin, hair, tissue, blood, plasma, cells, sweat and urine.

The term "cancer", as used herein, is defined as proliferation of cells whose unique trait—loss of normal controls—results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer.

As used herein, the term "carrier molecule" refers to any molecule that is chemically conjugated to the antigen of interest that enables an immune response resulting in antibodies specific to the native antigen.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "compound," as used herein, refers to a polypeptide, an isolated nucleic acid, or other agent used in the method of the invention.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell is a cell being examined.

A "pathoindicative" cell is a cell which, when present in a tissue, is an indication that the animal in which the tissue is located (or from which the tissue was obtained) is afflicted with a disease or disorder.

A "pathogenic" cell is a cell which, when present in a tissue, causes or contributes to a disease or disorder in the animal in which the tissue is located (or from which the tissue was obtained).

A tissue "normally comprises" a cell if one or more of the cell are present in the tissue in an animal not afflicted with a disease or disorder.

As used herein, a "derivative" of a compound refers to a chemical compound that may be produced from another compound of similar structure in one or more steps, as in replacement of H by an alkyl, acyl, or amino group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

A "fragment" or "segment" is a portion of an amino acid sequence, comprising at least one amino acid, or a portion of a nucleic acid sequence comprising at least one nucleotide.

The terms "fragment" and "segment" are used interchangeably herein.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCCS' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

By the term "immunizing a subject against an antigen" is meant administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of the antigen.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein when referring to a function, refers to the ability of a compound of the invention to reduce or impede a described function. Preferably, inhibition is by at least 10%, more preferably by at least 25%, even more preferably by at least 50%, and most preferably, the function is inhibited by at least 75%. When the term "inhibit" is used more generally, such as "inhibit Factor I", it refers to inhibiting expression, levels, and activity of Factor I.

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

As used herein "injecting, or applying, or administering" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

A "recombinant polypeptide" is one which is produced upon expression of a recombinant polynucleotide.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

By the term "vaccine," as used herein, is meant a composition which when inoculated into a subject has the effect of stimulating an immune response in the subject, which serves to fully or partially protect the subject against a condition, disease or its symptoms. In one aspect, the condition is cancer. The term vaccine encompasses prophylactic as well as therapeutic vaccines. A combination vaccine is one which combines two or more vaccines, or two or more compounds or agents.

EMBODIMENTS

In one embodiment, the invention provides a composition useful as a therapeutic for treating cancer or as a vaccine for preventing cancer in a subject in need thereof. In one aspect, the cancer is selected from the group consisting of melanoma, lung cancer, MMMT, bladder cancer, ovarian cancer, uterine cancer, endometrial cancer, breast cancer, head and neck cancer, liver cancer, pancreatic cancer, esophageal cancer, stomach cancer, cervical cancer, prostate cancer, adrenal cancer, lymphoma, leukemia, salivary gland cancer, bone cancer, brain cancer, cerebellar cancer, colon cancer, rectal cancer, colorectal cancer, oronasopharyngeal cancer, NPC, kidney cancer, skin cancer, basal cell carcinoma, hard palate carcinoma, squamous cell carcinoma of the tongue, meningioma, pleomorphic adenoma, astrocytoma, chondrosarcoma, cortical adenoma, hepatocellular carcinoma, pancreatic cancer, squamous cell carcinoma, and adenocarcinoma. In one aspect, the cancer is melanoma.

In one aspect, the therapeutic composition is useful as a vaccine. In one aspect, the composition comprises an effective amount of one or more peptides, or variants, homologs, or fragments thereof, said peptides comprising an amino acid sequence selected from the group consisting of SEQ ID NOs: 1, 2, 3, 4, 5, 6, 7, and 8 (the long peptides), and in some cases the composition further comprises at least at one of the short peptides selected from the group having SEQ ID NOs: 9, 10, 11, 12, 13, 14, 15, 16, 17, 18, 19, 20, and 21, wherein the variant, fragment, or homolog has the desired properties and effect. In one aspect, when the long peptides SEQ ID NOs:1, 2, 3, 4, 5, 6, 7, and 8 are used, although, typically, when 8 is used 1 is not and when 1 is used 8 is not, because there is only one amino acid difference between SEQ ID NOs:1 and 8.

When the seven peptides of SEQ ID NOs:2-8 are used, the cocktail or vaccine will be referred to as LPV7. As described above, of the two similar peptides (SEQ ID NOs:1 and 8), typically 8 will be used and LPV7 will include SEQ ID NOs:2-8. When the peptide have the amino acid sequence of SEQ ID NO:1 is used instead of SEQ ID NO:8, the cocktail will referred to as $LPV7_1$ or will list all sequences. In one embodiment, when the cocktail consists of six peptides and the six peptides are SEQ ID NOs:3-8, the cocktail is referred to as LPV6 herein. Other cocktails will be referred to according the SEQ ID NOs: of the specific peptides being used.

Despite the peptide selection based on the criteria described herein, one of ordinary skill in the art will appreciate that not all peptides are easily prepared. For example, it is sometimes difficult to achieve adequate purity, or solubility, and one peptide was found to work better by removing the C-terminal proline residue of SEQ ID NO:1 (FTIPYWDWRDAEKSDICTDEYMGGQHPTNP) to arrive at SEQ ID NO:8 (FTIPYWDWRDAEKSDICTDEYMGGQHPTN), a deletion fragment of SEQ ID NO:1. However, both can be used. Thus, several alternate sequences have been and will be selected for further use as well. The alternative sequences already prepared were tested for their solubility in aqueous solutions and for their ability to be recognized by human T cells in vitro. The present application further discloses compositions and methods for solubilizing them in solution with appropriate pH to enable sterile filtration to create a drug for human use.

The methods and compositions of the invention encompass multiple regimens and dosages for administering the peptides of the invention for use in preventing and treating cancer. For example, a subject can be administered a combination of peptides of the invention once or more than once. The frequency and number of doses can vary based on many parameters, including the age, sex, and health of the subject. In one embodiment, up to 50 doses are administered. In another embodiment, up to 40 doses are administered, and in another up to 30 doses are administered. In yet another embodiment, up to 20 doses are administered, and in another up to 10 doses are administered. In one embodiment, 5-10 doses are administered. In one aspect, 5, 6, 7, 8, 9, or 10 doses can be administered.

SEQ ID NOs:16-21 are short peptides found in Table 1 and discussed in the Background, not long peptides as disclosed and used herein. However, the present invention encompasses the use of combinations of effective peptides other than just the long peptides disclosed herein. For example, the short peptides having SEQ ID NOS:9-21 can be used in combination with the long peptide vaccine combinations disclosed herein.

In one embodiment, the peptides are administered daily, in another weekly, and in another, monthly. Treatment periods may be for a few days, or about a week, or about several weeks, or for several months. Follow-up administration or boosters can be used as well and the timing of that can be varied.

The amount of peptide administered per dose can vary as well. For example, in one embodiment the compositions and methods of the invention include a range of peptide amounts between about 10 micrograms of each peptide per dose to about 10,000 micrograms of peptide per dose. In one aspect, the number of micrograms is the same for each peptide. In another aspect, the number of micrograms is not the same for each peptide. In another embodiment, the range of amounts of each peptide administered per dose is from about 20 micrograms to about 1,000 micrograms. In another aspect, it is from about 50 micrograms to about 500 micrograms. In yet another aspect, it is from about 75 micrograms to about 400 micrograms. In a further aspect, it is from about 100 micrograms to about 300 micrograms, and in another aspect from about 150 micrograms to about 250 micrograms. In one embodiment, about 300 micrograms of each peptide is used per dose per treatment.

Subjects can be monitored before and after peptide administration for antibody levels against the peptides being administered and by monitoring T cell responses, including CD4+ and CD8+. Methods for these tests are routinely used in the art and are either described herein or, for example, in publications cited herein.

Although a vaccine composition or cocktail of peptides is described herein, when more than one peptide is administered, each different peptide can be administered separately. When a vaccine composition is administered more than once to a subject, the dose of each peptide may vary per administration.

In one embodiment, a vaccine composition of the invention is useful for treating and preventing cancers expressing the proteins gp100, MAGE-A1, MAGE-A3, and MAGE-A10.

To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters. Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation," a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($-NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for homologs of proteins and peptides. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on protein function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Homologs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein or peptide obtained as described herein may be purified by following known procedures for protein purification, wherein an immunological, enzymatic, or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

Vaccines and Immunogens

In one embodiment, the invention relates to methods and reagents for immunizing and treating a subject with at least one peptide of the invention such as a peptide having an amino acid sequence of SEQ ID NOs:1-21 and fragments and homologs thereof. Long peptides of the invention include SEQ ID NOs:1-8 and fragments and homologs thereof. In one embodiment, two or more peptides are used. In one embodiment seven peptides are used. In one embodiment, six peptides are used. In one aspect, the six peptides are those having SEQ ID NOs:3-8 (LPV6) In one aspect, the seven peptides are SEQ ID NOs:1-7, and in another 2-8. In one aspect, the at least one peptide elicits specific cellular and humoral immune-responses against such specific antigens.

One of ordinary skill in the art will appreciate that when more than one peptide is used that they do not necessarily have to be administered in the same pharmaceutical composition at the same time, and that multiple injections can also be used. When multiple injections are used they can be administered, for example, in a short sequence such as one right after the other or they can be spaced out over predetermined periods of time, such as every 5 minutes, every 10 minutes, every 30 minutes, etc. Of course, administration can also be performed by administering a pharmaceutical comprising all components to be administered, such as a cocktail comprising seven peptides of the invention. It can also be appreciated that a treatment regimen may include more than one round of injections, spaced over time such as weeks or months, and can be altered according to the effectiveness of the treatment on the particular subject being treated.

The invention provides multiple methods of using specifically prepared immunogens, for example, in fresh or lyophilized liposome, proper routes of administration of the immunogen, proper doses of the immunogen, and specific combinations of heterologous immunization including DNA priming in one administration route followed by liposome-mediated protein antigen boost in a different route to tailor the immune responses in respects of enhancing cell mediated immune response, cytokine secretion, humoral immune response, especially skewing T helper responses to be Th1 or a balanced Th1 and Th2 type. For more detail, see Klinefelter (U.S. patent application Ser. No. 11/572,453, which claims priority to international patent application PCT/US2005/026102).

A homolog herein is understood to comprise an immunogenic peptide having at least 70%, preferably at least 80%, more preferably at least 90%, still more preferably at least 95%, still more preferably at least 98% and most preferably at least 99% amino acid sequence identity with the peptides mentioned above and is still capable of eliciting at least the immune response obtainable thereby. A homolog or analog may herein comprise substitutions, insertions, deletions, additional N- or C-terminal amino acids, and/or additional chemical moieties, such as carbohydrates, to increase stability, solubility, and immunogenicity.

In one embodiment of the invention, the present immunogenic polypeptides as defined herein, are glycosylated. Without wishing to be bound by any particular theory, it is hypothesized herein that by glycosylation of these polypeptides the immunogenicity thereof may be increased. Therefore, in one embodiment, the aforementioned immunogenic polypeptide as defined herein before, is glycosylated, having a carbohydrate content varying from 10-80 wt %, based on the total weight of the glycoprotein or glycosylated polypeptide. Said carbohydrate content ranges can be from 15-70 wt %, or from 20-60 wt %. In another embodiment, said glycosylated immunogenic polypeptide comprises a glycosylation pattern that is similar to that of the peptides of the human that is treated. It is hypothesized that this even further increases the immunogenicity of said polypeptide. Thus, in one embodiment, the immunogenic polypeptide comprises a glycosylation pattern that is similar to that of the corresponding glycoprotein.

In one embodiment, the source of a peptide comprises an effective amount of at least one immunogenic peptide selected from the peptides described herein, and immunologically active homologs thereof and fragments thereof, or a nucleic acid sequence encoding said immunogenic peptide.

In one embodiment, the present method of immunization comprises the administration of a source of immunogenically active peptide fragments, said peptide fragments being selected from the peptide fragments and/or homologs thereof as defined herein before. Peptides having a length between 18 and 45 amino acids have been observed to provide superior immunogenic properties as is described in WO 02/070006.

Peptides may advantageously be chemically synthesized and may optionally be (partially) overlapping and/or may also be ligated to other molecules, peptides, or proteins. Peptides may also be fused to form synthetic proteins, as in Welters et al. (Vaccine. 2004 Dec. 2; 23(3):305-11). It may also be advantageous to add to the amino- or carboxy-terminus of the peptide chemical moieties or additional (modified or D-) amino acids in order to increase the stability and/or decrease the biodegradability of the peptide. To improve immunogenicity, immuno-stimulating moieties may be attached, e.g. by lipidation or glycosylation. To enhance the solubility of the peptide, addition of charged or polar amino acids may be used, in order to enhance solubility and increase stability in vivo.

For immunization purposes, the aforementioned immunogenic peptides of the invention may also be fused with proteins, such as, but not limited to, tetanus toxin/toxoid, diphtheria toxin/toxoid or other carrier molecules. The polypeptides according to the invention may also be advantageously fused to heatshock proteins, such as recombinant endogenous (murine) gp96 (GRP94) as a carrier for immunodominant peptides as described in (references: Rapp U K and Kaufmann S H, Int Immunol. 2004 April; 16(4):597-605; Zugel U, Infect Immun. 2001 June; 69(6):4164-7) or fusion proteins with Hsp70 (Triebel et al; WO9954464).

The individual amino acid residues of the present immunogenic (poly)peptides of the invention can be incorporated in the peptide by a peptide bond or peptide bond mimetic. A peptide bond mimetic of the invention includes peptide backbone modifications well known to those skilled in the art. Such modifications include modifications of the amide nitrogen, the alpha carbon, amide carbonyl, complete replacement of the amide bond, extensions, deletions, or backbone crosslinks. See, generally, Spatola, Chemistry and Biochemistry of Amino Acids, Peptides and Proteins, Vol. VII (Weinstein ed., 1983). Several peptide backbone modifications are known and can be used in the practice of the invention.

Amino acid mimetics may also be incorporated in the polypeptides. An "amino acid mimetic" as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to elicit an immune response. Amino acid mimetics may include non-protein amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) Ann. Repts. Med. Chem. 24:243-252.

In one embodiment, the present method comprises the administration of a composition comprising one or more of the present immunogenic peptides as defined herein above, and at least one excipient. Excipients are well known in the art of pharmacy and may for instance be found in textbooks such as Remington's pharmaceutical sciences, Mack Publishing, 1995.

The present method for immunization may further comprise the administration, and in one aspect, the co-administration, of at least one adjuvant. Adjuvants may comprise any adjuvant known in the art of vaccination or composition for eliciting an immune response and may be selected using textbooks like Current Protocols in Immunology, Wiley Interscience, 2004.

Adjuvants are herein intended to include any substance or compound that, when used, in combination with an antigen, to immunize a human or an animal, stimulates the immune system, thereby provoking, enhancing or facilitating the immune response against the antigen, preferably without generating a specific immune response to the adjuvant itself. In one aspect, adjuvants can enhance the immune response against a given antigen by at least a factor of 1.5, 2, 2.5, 5, 10, or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens. The adjuvant of the invention will usually be a compound that is foreign to a human, thereby excluding immunostimulatory compounds that are endogenous to humans, such as e.g. interleukins, interferons, and other hormones.

A number of adjuvants are well known to one of ordinary skill in the art. Suitable adjuvants include, e.g., incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxy-phosphoryloxy)-ethylamine (CGP 19835A, referred to as MTP-PE), DDA (2 dimethyldioctadecylammonium bromide), polyIC, Poly-A-poly-U, RIBI™, GERBU™, Pam3™, Carbopol™, Specol™, Titermax™, tetanus toxoid, diphtheria toxoid, meningococcal outer membrane proteins, diphtheria protein $CRM_{197}$. Preferred adjuvants comprise a ligand that is recognized by a Toll-like-receptor (TLR) present on antigen presenting cells. Various ligands recognized by TLR's are known in the art and include e.g. lipopeptides (see, e.g., WO 04/110486), lipopolysaccharides, peptidoglycans, liopteichoic acids, lipoarabinomannans, lipoproteins (from *mycoplasma* or spirochetes), double-stranded RNA (poly I:C), unmethylated DNA, flagellin, CpG-containing DNA, and imidazoquinolines, as well derivatives of these ligands having chemical modifications.

The methods of immunization of the present application further encompass the administration, including the co-administration, of a CD40 binding molecule in order to enhance a CTL response and thereby enhance the therapeutic effects of the methods and compositions of the invention. The use of CD40 binding molecules is described in WO 99/61065, incorporated herein by reference. The CD40 binding molecule is preferably an antibody or fragment thereof or a CD40 Ligand or a variant thereof, and may be added separately or may be comprised within a composition according to the current invention. Such effective dosages will depend on a variety of factors including the condition and general state of health of the patient. Thus, dosage regimens can be determined and adjusted by trained medical personnel to provide the optimum therapeutic or prophylactic effect.

In the present method, the one or more immunogenic polypeptides are typically administered at a dosage of about 1 ug/kg patient body weight or more at least once. Often dosages are greater than 10 μg/kg. According to the present invention, the dosages preferably range from 1 μg/kg to 1 mg/kg.

In one embodiment typical dosage regimens comprise administering a dosage of 1-1000 ug/kg, more preferably 10-500 μg/kg, still more preferably 10-150 μg/kg, once, twice or three times a week for a period of one, two, three, four or five weeks. According to one embodiment, 10-100 μg/kg is administered once a week for a period of one or two weeks.

The present method, in one aspect, comprises administration of the present immunogenic polypeptides and compositions comprising them via the injection, transdermal, or oral route. In another, embodiment of the invention, the present method comprises vaginal administration of the present immunogenic polypeptides and compositions comprising them.

Another aspect of the invention relates to a pharmaceutical preparation comprising as the active ingredient the present source of a polypeptide as defined herein before. More particularly pharmaceutical preparation comprises as the active ingredient one or more of the aforementioned immunogenic peptides, homologues thereof and fragments of said peptides and homologs thereof, or, alternatively, a gene therapy vector as defined herein above.

The present invention further provides a pharmaceutical preparation comprising one or more of the immunogenic peptides of the invention. The concentration of said peptides in the pharmaceutical composition can vary widely, i.e., from less than about 0.1% by weight, usually being at least about 1% by weight to as much as 20% by weight or more.

The composition may comprise a pharmaceutically acceptable carrier in addition to the active ingredient. The pharmaceutical carrier can be any compatible, non-toxic substance suitable to deliver the immunogenic polypeptides or gene therapy vectors to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

In one embodiment, the present pharmaceutical composition comprises an adjuvant, as defined in more detail herein before. Adjuvants useful for incorporation in the present composition are preferably selected from the group of ligands that are recognized by a Toll-like-receptor (TLR) present on antigen presenting cells, including lipopeptides, lipopolysaccharides, peptidoglycans, liopteichoic acids, lipoarabinomannans, lipoproteins (from *mycoplasma* or spirochetes), double-stranded RNA (poly I:C), unmethylated DNA, flagellin, CpG-containing DNA, and imidazoquinolines, as well derivatives of these ligands having chemical modifications. The routineer will be able to determine the exact amounts of anyone of these adjuvants to be incorporated in the present pharmaceutical preparations in order to render them sufficiently immunogenic. According to another preferred embodiment, the present pharmaceutical preparation may comprise one or more additional ingredients that are used to enhance CTL immunity as explained herein before. According to a particularly preferred embodiment the present pharmaceutical preparation comprises a CD40 binding molecule.

Methods of producing pharmaceutical compositions comprising polypeptides are described, for example, in U.S. Pat. Nos. 5,789,543 and 6,207,718. The preferred form depends on the intended mode of administration and therapeutic application.

In one embodiment, the present immunogenic peptides are administered by injection. The parenteral route for administration of the polypeptide is in accordance with known methods, e.g., injection or infusion by intravenous, intraperitoneal, intramuscular, intra-arterial, subcutaneous, or intralesional routes. The protein or polypeptide may be administered continuously by infusion or by bolus injection. In one embodiment, a composition for intravenous infusion could be made up to contain 10 to 50 ml of sterile 0.9% NaCl or 5% glucose optionally supplemented with a 20% albumin solution and between 10 µg and 50 mg, preferably between 50 µg and 10 mg, of the polypeptide. A typical pharmaceutical composition for intramuscular injection would be made up to contain, for example, 1-10 ml of sterile buffered water and between 10 µg and 50 mg, preferably between 50 ug and 10 mg, of the polypeptide of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

For convenience, immune responses are often described in the present invention as being either "primary" or "secondary" immune responses. A primary immune response, which is also described as a "protective" immune response, refers to an immune response produced in an individual as a result of some initial exposure (e.g., the initial "immunization") to a particular antigen. Such an immunization can occur, for example, as the result of some natural exposure to the antigen (for example, from initial infection by some pathogen that exhibits or presents the antigen). Alternatively, the immunization can occur because of vaccinating the individual with a vaccine containing the antigen. For example, the vaccine can be a vaccine comprising one or more antigenic epitopes or fragments of the peptides of the invention.

Amino Acid Substitutions

In certain embodiments, the disclosed methods and compositions may involve preparing peptides with one or more substituted amino acid residues. In various embodiments, the structural, physical and/or therapeutic characteristics of peptide sequences may be optimized by replacing one or more amino acid residues.

In one embodiment, the invention encompasses the substitution of a serine or an alanine residue for a cysteine residue in a peptide of the invention. Support for this includes what is known in the art. For example, see the following citation for justification of such a serine or alanine substitution: Kittlesen et al., 1998 Human melanoma patients recognize an HLA-A1-restricted CTL epitope from tyrosinase containing two cysteine residues: implications for tumor vaccine development J Immunol., 60, 2099-2106.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of Alkyl-Substituted Hydrophobic Amino Acids:

including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of Aromatic-Substituted Hydrophobic Amino Acids:

including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of Amino Acids Containing Basic Functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of Acidic Amino Acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of Side Chain Amide Residues: including asparagine, glutamine, and alkyl or aromatic substituted derivatives of asparagine or glutamine.

Substitution of Hydroxyl Containing Amino Acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

The invention is also directed to methods of administering the compounds of the invention to a subject.

Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

The present invention is also directed to pharmaceutical compositions comprising the peptides of the present invention. More particularly, such compounds can be formulated as pharmaceutical compositions using standard pharmaceutically acceptable carriers, fillers, solublizing agents and stabilizers known to those skilled in the art.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day. Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

Compounds which are identified using any of the methods described herein may be formulated and administered to a subject for treatment of the diseases disclosed herein.

The invention encompasses the preparation and use of pharmaceutical compositions comprising a compound useful for treatment of the conditions, disorders, and diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively).

Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil in water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may also be prepared, packaged, or sold in a formulation suitable for rectal administration, vaginal administration, parenteral administration The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example.

Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self propelling solvent/powder dispensing container such as a device comprising the active ingredient dissolved or suspended in a low-boiling propellant in a sealed container.

Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein. A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference. Typically, dosages of the compound of the invention which may be administered to an animal, preferably a human, range in amount from 1 µg to about 100 g per kilogram of body weight of the subject. While the precise dosage administered will vary depending upon any number of factors, including but not limited to, the type of animal and type of disease state being treated, the age of the animal and the route of administration. In one embodiment, the dosage of the compound will vary from about 10 µg to about 10 g per kilogram of body weight of the animal. In another embodiment, the dosage will vary from about 10 mg to about 1 g per kilogram of body weight of the subject.

The compound may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, etc.

The invention also includes a kit comprising a compound of the invention and an instructional material which describes administering the composition to a cell or a tissue of a subject. In another embodiment, this kit comprises a (preferably sterile) solvent suitable for dissolving or suspending the composition of the invention prior to administering the compound to the subject. The invention also provides an applicator, and an instructional material for the use thereof.

Multiple techniques for measuring proteins and peptides are known in the art or described herein and can use in the practice of the invention. These include, but are not limited to, for example:

Electrochemiluminescent immunoassay;

Bioluminsescent Immunoassay (for example, with use of apoaequorin and oelenterazine);

Luminescent oxygen channeling immunoassay (LOCI);

The Erenna Immunoassay System (a modified microparticle-based sandwich immunoassay with single-molecule counting);

Nanoparticle Immunoassay: nano-particles, spheres, or tubes as solid phases upconverting phosphor nanoparticle using antiStokes shift quantum dot immunoassay (Heterogeneous immunoassay in which a nanometer-sized (less than 10 nm) semiconductor quantum dot is used as a label. A quantum dot is a highly fluorescent nanocrystal composed of CdSe, CdS, ZnSe, InP, or InAs or a layer of ZnS or CdS on, for example, a CdSe core);

Fluorescence Excitation Transfer Immunoassay;

ImmunoPCR Immunoassay;

Solid Phase, Light-Scattering Immunoassay: Indium spheres are coated on glass to measure an antibody binding to an antigen. Binding of antibodies to antigens increases dielectric layer thickness, which produces a greater degree of scatter than in areas where only an antigen is bound. Quantitation is achieved by densitometry; and Surface Effect Immunoassay: with antibody immobilized on the surface of a waveguide (a quartz, glass, or plastic slide, or a gold- or silver-coated prism), and binding of antigen measured directly by total internal reflection fluorescence, surface plasmon resonance, or attenuated total reflection.

Without further description, it is believed that one of ordinary skill in the art can, using the preceding description and the following illustrative examples, make and utilize the compounds of the present invention and practice the claimed methods. The following examples therefore, specifically point out the preferred embodiments of the present invention, and are not to be construed as limiting in any way the remainder of the disclosure.

EXAMPLES

Long peptide vaccine compositions of the invention comprising multiple long peptides, such as LPV6 and LPV7, are cocktails of 6 or 7 long (approximately 30-mer) peptides from cancer-testis antigens (CTA) & melanocytic differentiation proteins (MDP), listed in Table 2. LPV6 and LPV7 comprises 6 or 7 peptides, respectively, from CTA and MDA that have been designed to incorporate each of 6 or 7 well-defined and immunogenic minimal epitopes recognized by melanoma-reactive T cells, and to be stable and soluble.

In HLA-A2 transgenic mice, vaccination was tested with short (SEQ ID NO:11) and long peptides (SEQ ID NO:3) encompassing YMDGTMSQV (tyrosinase$_{369-377}$) (SEQ ID NO:11) listed in Table 2: the long peptide induced a 5- to 10-fold higher immune response to the short peptide than vaccination with that short peptide itself (FIG. 1).

Figure 2:
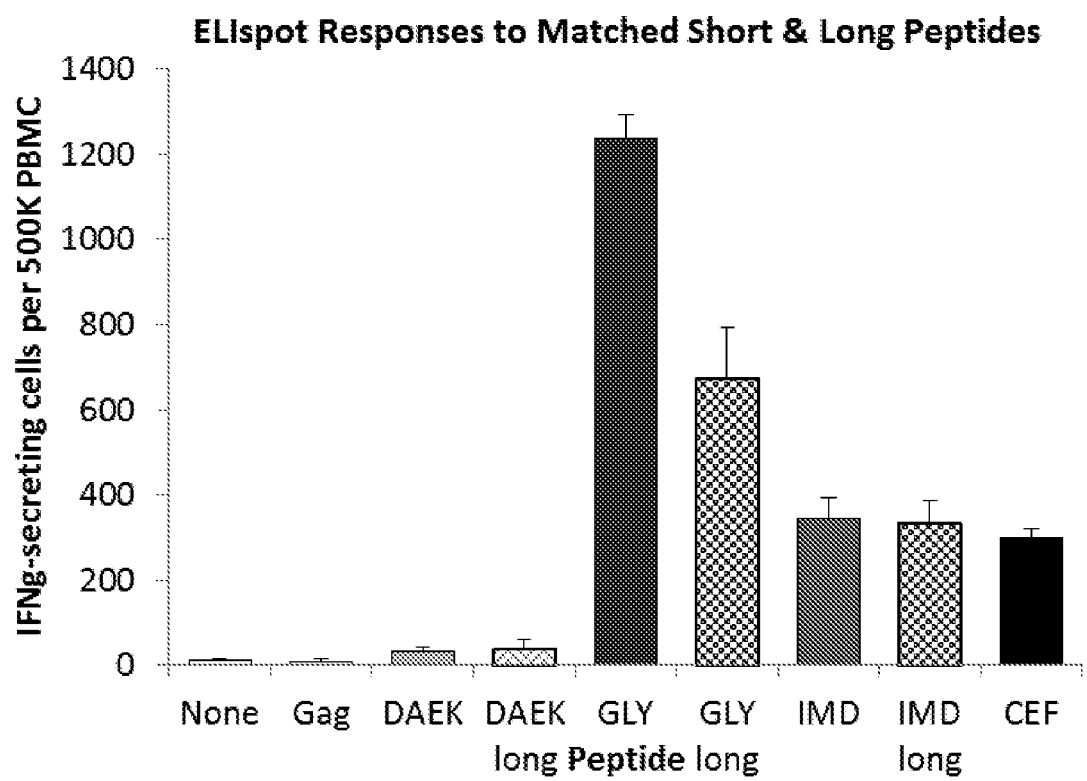
FIG. 2. PBMC from an HLA-A1+/A2+ patient vaccinated with 12MP were assayed in 20 hr direct ELISpot against short and long versions of tyrosinase$_{240-251S}$ (DAEK, green), MAGE-A10$_{254-262}$ (GLY, blue), and gp100$_{209-217-2M}$ (IMD, red) for IFN-gamma secreting cells. The ratio of reactivities of long (hatched bars) to short (solid bars) peptides are 1.1, 0.55, and 0.96, respectively. See Table 2 for sequences of each short and long peptide used in FIG. 2.

We have also tested whether this and other long peptides can be cross-presented, assaying reactivity of PBMC from patients previously vaccinated with 12MP, who have known CD8$^+$ T cell reactivity patterns. Example data are shown in FIG. 2, and summary data are provided in Table 3. For all of the peptides tested by ELIspot assay in this way, one or more patients had T cells responsive to the long peptides. Lower reactivity to the long peptides is likely due in part to recognition of short peptides by low avidity T cells induced by vaccination in some patients, and due to the limited number of effective antigen-presenting cells in PBMC, capable of processing and presenting the peptide epitopes, in some patients. In summary, even in this assay, which is not enriched for professional APC, all of the long peptides tested can be cross-presented as the minimal defined epitope.

The use of 12MP has been described previously (Slingluff et al., 2007, Clin. Cancer Res. 13:6386). 12MP stands for "12 melanoma peptides" and refers to the mixture of 12 short peptides with which we have substantial experience. Specifically, 12MP includes the 7 short peptides (SEQ ID NO: 9-15) on which the long peptides of the present invention are based plus 5 other peptides.

Incorporation of Epitopes to Stimulate CD4 T Cells.

The long peptides to be used in this project contain epitopes for CD4$^+$ T cells. Vaccination with NY-ESO-1$_{79-108}$ induces CD4 T cell responses, and the other peptides are expected to do the same, and thus to license DC locally at the VSME and VDLN.

Formulation of Long Peptide Vaccines, Including LPV6 and LPV7

Vaccines will use the long peptides listed in Table 2, or effective homologs or fragments thereof. When the cocktail consist of the seven peptides having SEQ ID NOs:2-8 it will be referred to as LPV7. When the cocktail consists of the six peptides having SEQ ID NOs:3-8, it will be referred to as LPV6. Other mixtures or combinations not specifically named will be referred to, for example, by the particular peptides (SEQ ID NOs) in the cocktail or to be used as part of the regimen. These peptides encompass several well-defined epitopes restricted by HLA-A1, A2, A3, A11, and A31. In our experience, this represents 85-90% of the melanoma patient population.

Solubilization of Long Peptides:

Vaccines are prepared by solubilization of each peptide in aqueous solutions, then sterile filtration, mixing, and vialing at 600 mcg per vial. Each of these peptides has multiple (4-9, median 6) polar residues (D, E, H, K, and R), which support solubility.

The long peptides (SEQ ID NOs:1-8) presented major solubility issues when being prepared. They were found to have unique solubility properties. Notably, depending on the particular peptide the pH range for solubility ranged from about 4 to about 12, with different net solubility. Although to some degree it is routine to adjust pH and concentration when determining solubility, many peptides are considered insoluble in aqueous solution, and it is not trivial to solubilize those proteins.

For each of peptides 1, 5, and 7B (SEQ ID NOs:1, 5, and 7, respectively), (or SEQ ID NO:8 if it is used instead of SEQ ID NO:1) 1 gram of peptide is solubilized in 50 ml water+5 ml of sodium bicarbonate solution (8.4% USP), for a final volume of 55 ml and 0.8% NaHCO3, at 18.2 mg/ml. Each is a clear colorless solution at pH 8-9. Peptide 2C (SEQ ID NO:2) can also be prepared using these conditions. It is then sterile-filtered. One gram of peptide #4 (SEQ ID NO:4) will be solubilized in 50 ml water at 20 mg/ml. This is a clear colorless solution at pH 4-5. It is then sterile-filtered. These peptides, 1, 4, 5, and 7B (SEQ ID NOs:1, 4, 5, and 7, respectively), will be mixed to produce a solution of these 4 peptides, each at 1 mg in a total volume of 270 ml (4.65 mg/ml), at pH ~8.5.

The solubilization regimen was difficult to establish for the 8 long peptides. For example, for peptide 7B (SEQ ID NO:7), it was found to be soluble at a reasonable concentration and pH, but was very viscous. It is disclosed herein that increasing the pH above 8.5 with a base such as NaOH decreased the viscosity, allowing the solution to be sterile-filtered.

One gram of peptide #6 (SEQ ID NO:6) is solubilized in 100 ml water at 10 mg/ml. This is a clear colorless solution at pH 4-5. It is sterile-filtered.

One gram of peptide #3 (SEQ ID NO:3) will be solubilized in water plus 10N NaOH at 2 mg/ml. This is a clear colorless solution at approximately pH 12. Sodium hydroxide (GMP grade) and water will be added to bring this to pH 12, at which point this will be a clear colorless solution. We have verified that the peptide is stable at this pH and is not hydrolyzed or degraded. It will be sterile-filtered. This regimen for solubilization required significant effort to establish because of solubility issues of peptide #3 (SEQ ID NO:3). The procedure required adding NaOH to bring the pH up to 12, which of course increases the risk of alkaline hydrolysis. However, it was found that the peptide was still intact.

These 3 sterile solutions will be combined and will be brought up to a concentration of 600 mcg/ml of each peptide using sterile water, lactated ringer's solution or normal saline solution. The pH of the mixture will be about 8-8.50, for a concentration of 600 micrograms per ml of each peptide. This will be slightly cloudy as peptides 3 and 6 fall out of solution at the pH of approximately 8 in the final suspension.

For peptide sequences #3 and #7 (7B) in particular, we had significant challenges—for #3, it required adding NaOH (sodium hydroxide) to bring the pH to 12; at pH 12, there is some risk of alkaline hydrolysis, but we have confirmed that hydrolysis is not an issue and the peptide is intact. For peptide #7 (7B), it is soluble at reasonable concentration, at pH 8.5 but was very viscous when I test-solubilized it; however, when we did large scale solubilization yesterday for the trial, it was so very viscous that resembled a hair gel, and it would not have been possible to sterile-filter it. We figured out then to increase the pH further, again with NaOH, and I didn't know for sure if it would work; it did.

See Tables 4-5 for more details for solublizing specific peptides of the invention. All peptides are also submitted for quality assurance studies and amino acid analysis, then combined as acidic (such as peptides 4 and 6) or basic (such as peptides 1, 3, 5, 7B) solutions, respectively, and then further tested for definitive quality assurance and validation studies. For example, peptide 7B (SEQ ID NO: 7) was prepared by adding 45 ml water, 6 ml NaHCO3 (8.4%), 30 ml of Lactated Ringer's Solution (LR), for a total volume of 81 ml (See Table 5). Then, 2 ml was transferred out of this 81 ml (for test changes in pH); so the net volumes left in the original tube were: Water 43.89 ml; NaHCO3 5.85 ml; LR 29.26 ml=total 79 ml (remaining peptide=585.185 mg). To that was added 5 ml of 0.2 N NaOH, yielding a total of 84 ml at 6.9665 mg/ml.

Solutions are also filter-sterilized using 0.2 micron filters and aliquots are preserved for testing using HPLC, AAA, etc.

The various sterile solutions can also be modified, depending on whether different peptides are being used for the cocktail.

The solutions to be used for treatment are then vialed into borosilicate vials with stoppers, for single use, at 0.5-1.0 ml per vial. The final vials of peptide in aqueous solution will be stored at −80° C.

Appropriate quality assurance tests will be performed on the final product. Quality assurance testing will include mass spectrometry, HPLC, and amino acid analysis for purity and identity, as well as sterility testing, general safety testing in accord with CFR guidelines. We will follow guidelines for quality assurance studies to assure stability of the peptide preparation over time during the trial.

TABLE 1

Defined peptide epitopes in NY-ESO-1$_{79-108}$

| Peptide | Residues in NY-ESO-1 | HLA-restriction | HLA frequency among melanoma patients |
|---|---|---|---|
| Class I MHC-restricted epitopes for CD8$^+$ T cells | | | |
| MPFATPMEA SEQ ID NO: 16 | 94-102 | B35/B51 | 15%/7% |
| LAMPFATPM SEQ ID NO: 17 | 92-100 | Cw3 | 15% |
| ARGRESRLL SEQ ID NO: 18 | 80-88 | Cw6 | 18% |
| Class II MHC-restricted epitopes for CD4$^+$ T cells | | | |
| EFYLAMPFATPM SEQ ID NO: 19 | 89-100 | DR1 | 19% |
| PFATPMEAERARR SEQ ID NO: 20 | 95-107 | DR4 | 24% |
| LLEFYLAMPFATPM SEQ ID NO: 21 | 87-100 | DR9 | 4% |

TABLE 2

Seven Long Melanoma Peptides and corresponding defined epitopes restricted by MHC Class I (each amino acid is represented by its standard single letter abbreviation)

| Defined HLA | Some Long Peptides for LPVs for the present proposal | | Short Peptide Epitopes for CD8 cells | |
|---|---|---|---|---|
| HLA-A1 | FTIPYWDWR<u>DAEKSDICTDEY</u>MGGQHPTNP SEQ ID NO: 1 | Tyrosinase 231-260 S* (30) | DAEKSDICTDE SEQ ID NO: 9 | Tyrosinase 240-251S* |
| | SKASSSLQLVFGIEL<u>MEVDPIGHLY</u>IFAT SEQ ID NO: 2 | MAGE-A3 152-180 (29) | EVDPIGHLY SEQ ID NO: 10 | MAGE-A3 168-176 |
| HLA-A2 | SMHNALHI<u>YMDGTMSQV</u>QGSANDPIFLLHH SEQ ID NO: 3 | Tyrosinase ♦ 361-390 (30) | YMDGTMSQV SEQ ID NO: 11 | Tyrosinase 369-377 ♦ |
| | VPLAHSSSAFT<u>IMDQVPFSV</u>SVSQLRALDG SEQ ID NO: 4 | gp100 198-227 (30) | IMDQVPFSV SEQ ID NO: 12 | gp100 209-217-2M # |
| HLA-A3 | VIWEALNMMG<u>LYDGMEHL</u>IYGEPRKLLTQD SEQ ID NO: 5 | MAGE-A10 245-274 (30) | GLYDGMEHL SEQ ID NO: 13 | MAGE-A10 254-262 |
| | LLHLAVIG<u>ALLAVGATK</u>VPRNQDWLGVSRQL SEQ ID NO: 6 | gp100 9-39 (31) | ALLAVGATK SEQ ID NO: 14 | gp100 17-25 |
| HLA-A3, A11 | SREEEGPSTSCILE<u>SLFRAVITK</u>KVADLVG SEQ ID NO: 7 | MAGE-A1 82-111 (30) | SLFRAVITK SEQ ID NO: 15 | MAGE-A1 96-104 |

*substitution of S for C, residue 244;
♦ post-translational change of N to D, residue 371;
209-2M, substitution of M for T, position 210

TABLE 3

ELIspot responses to 7 long melanoma peptides by T-cells reactive to internal short peptide sequence

| Peptide no. | Some Long Peptides for the present trial (short peptide underlined) | T cell populations reactive to short peptide tested | No. (%) reactive to long peptide in 20 h ELIspot assay | Reactivity as proportion of reactivity to short peptide (mean) |
|---|---|---|---|---|
| 1 | FTIPYWDWR<u>DAEKSDICTDEY</u>MGG QHPTNP (SEQ ID NO: 1) | 4 | 1 (25%) | 113% |
| 2C | SKASSSLQLVFGIEL<u>MEVDPIGHLY</u>I FAT (SEQ ID NO: 2) | 3 | 2 (67%) | 153% |
| 3 | SMHNALHI<u>YMDGTMSQV</u>QGSAND PIFLLHH (SEQ ID NO: 3) | 2 | 1 (50%) | 62% |

TABLE 3 -continued

ELIspot responses to 7 long melanoma peptides by T-cells reactive to internal short peptide sequence

| Peptide no. | Some Long Peptides for the present trial (short peptide underlined) | T cell populations reactive to short peptide tested | No. (%) reactive to long peptide in 20 h ELIspot assay | Reactivity as proportion of reactivity to short peptide (mean) |
|---|---|---|---|---|
| 4 | VPLAHSSSAFTIMDQVPFSVSVSQL RALDG (SEQ ID NO: 4) | 6 | 6 (100%) | 91% |
| 5 | VIWEALNMMGLYDGMEHLIYGE PRKLLTQD (SEQ ID NO: 5) | 5 | 2 (40%) | 57% |
| 6 | LLHLAVIGALLAVGATKVPRNQDW LGVSRQL (SEQ ID NO: 6) | 9 | 1 (11%) | 9% |
| 7B | SREEEGPSTSCILESLFRAVITKKVA DLVG (SEQ ID NO: 7) | 11 | 9 (82%) | 10% |

TABLE 4

| Allele | Peptide ID UVA HITC | Peptide ID Polypeptide Group | Long Peptide (30-mers) in LPV6 for the present proposal Sequence (minimal epitope underlined) | Epitope (# residues) |
|---|---|---|---|---|
| HLA-A1 | 1 (8) | MPS-471 | FTIPYWDWRDAEKSDICTDEYMGGQHPTN (SEQ ID NO: 8) | Tyrosinase $_{231-259}$ $S^*$ (29) |
| HLA-A2 | 3 | MPS-458 | SMHNALHIYMDGTMSQVQGSANDPIFLLHH (SEQ ID NO: 3) | Tyrosinase $_{361-390D}$ ♦ (30) |
|  | 4 | MPS-459 | VPLAHSSSAFTIMDQVPFSVSVSQLRALDG (SEQ ID NO: 4) | gp100 $_{198-227-13M}$ $^\#$ (30) |
|  | 5 | MPS-460 | VIWEALNMMGLYDGMEHLIYGEPRKLLTQD (SEQ ID NO: 5) | MAGE-A10 $_{245-274}$ (30) |
| HLA-A3 | 6 | MPS-461 | LLHLAVIGALLAVGATKVPRNQDWLGVSRQL (SEQ ID NO: 6) | gp100 $_{9-39}$ (31) |
|  | 7B | MPS-462 | SREEEGPSTSCILESLFRAVITKKVADLVG (SEQ ID NO: 7) | MAGE-A1 $_{82-111}$ (30) |

TABLE 5

Solubilization of Long Peptides

| Peptide ID | Mass (mg) | Add solvents/buffers (ml) | | | | Features of final solution | | | | | |
|---|---|---|---|---|---|---|---|---|---|---|---|
| | | water | NaHCO$_3$ 8.4% | 0.2N NaOH | Lactated Ringer's | Final volume (ml) | Final conc. (mg/ml) | Final % NaHCO$_3$ | NaOH (N) | Appearance | Approx pH |
| 1 | 600 | 30 | 3 | — | — | 33 | 18.2 | 0.76 | — | Clear | 8.5 |
| 3 | 600 | 291.3 | 5.8 | 43.7 | — | 340.8 | 1.8 | 0.14 | 0.026 | Clear | 12 |
| 4 | 600 | 30 | — | — | — | 30 | 20.0 | — | — | Clear | 4 |
| 5 | 600 | 30 | 3 | — | — | 33 | 18.2 | 0.76 | — | Faint yellow translucent | 8.5 |
| 6 | 600 | 60 | — | — | — | 60 | 10.0 | — | — | Clear | 5 |
| 7B | 585.2 | 43.89 | 5.85 | 5 | 29.26 | 84 | 6.97 | 0.585 | 0.012 | Hazy, slightly viscous | 8.5-10 |

CONCLUSIONS

Recent data show that a peptide vaccine combined with existing therapy (interleukin-2) improves therapeutic response and progression-free survival of patients with advanced melanoma. Also, a protein and cellular vaccine for prostate cancer has been approved for use by the FDA (Sipileucel-T). Thus, cancer vaccines and immunogenic treatments are likely to become a part of cancer therapy generally.

However, short peptides have disadvantages and are associated with immune responses that decline over time. The use of long peptides protects the epitopes within them from being degraded in vivo, and ensures that the relevant T cell epitopes are presented by professional antigen presenting cells.

Thus, long peptides should increase durability of T cell responses, and improve the avidity of T cells responding to them. The impact is that this could dramatically improve the ability to control melanoma by a cancer vaccine.

This peptide vaccine may improve survival of patients with melanoma, when added to existing therapy. Over 60,000 patients are diagnosed with melanoma each year in the U.S. alone. There are approximately 1 million melanoma survivors, all of whom are at risk of future melanoma recurrence and melanoma-related death. These are the potential market for a therapeutic vaccine.

Another group of subjects that is an appropriate market includes those with high risk of melanoma: strong family history, many atypical moles, etc. This group would expand the potential market.

There also is a potential market in veterinary medicine, as dogs and horses get melanoma. There is a DNA vaccine approved for use in canine melanoma, but the present methodology and composition provides greater potential benefits as described herein. This could be competitive either in its current formulation or with modification to match the canine or equine homologues of the peptides.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Dunn G P, Ikeda H, Bruce A T et al. Interferon-gamma and cancer immunoediting. Immunol Res 2005; 32:231-245.
2. Shankaran V, Ikeda H, Bruce A T et al. IFNgamma and lymphocytes prevent primary tumour development and shape tumour immunogenicity. Nature 2001; 410:1107-1111.
3. Mihm M C, Jr., Clemente C G, Cascinelli N. Tumor-infiltrating lymphocytes in lymph node melanoma metastases: a histopathologic prognostic indicator and an expression of local immune response. Laboratory Investigation 1996; 74:43-47.
4. Bogunovic D, O'Neill D W, Belitskaya-Levy I et al. Immune profile and mitotic index of metastatic melanoma lesions enhance clinical staging in predicting patient survival. Proc Natl Acad Sci USA 2009; 106:20429-20434.
5. Gajewski T F. Failure at the effector phase: immune barriers at the level of the melanoma tumor microenvironment. Clin Cancer Res 2007; 13:5256-5261.
6. Yamshchikov G V, Barnd D L, Eastham S et al. Evaluation of peptide vaccine immunogenicity in draining lymph nodes and blood of melanoma patients. Int J Cancer 2001; 92:703-711.
7. Chianese-Bullock K A, Pressley J, Garbee C et al. MAGE-A1-, MAGE-A10-, and gp100-derived peptides are immunogenic when combined with granulocyte-macrophage colony-stimulating factor and montanide ISA-51 adjuvant and administered as part of a multipeptide vaccine for melanoma. J I 2005; 174:3080-3086.
8. Rosenberg S A, Yang J C, Restifo N P. Cancer immunotherapy: moving beyond current vaccines. Nat Med 2004; 10:909-915.
9. Slingluff C L, Jr., Petroni G R, Olson W et al. Helper T cell responses and clinical activity of a melanoma vaccine with multiple peptides from MAGE and melanocytic differentiation antigens. J Clin Oncol 2008; 26:4973-4980.
10. Schwartzentruber D J, Lawson D H, Richards J M et al. gp100 peptide vaccine and interleukin-2 in patients with advanced melanoma. N Engl J Med 2011; 364:2119-2127.
11. Schaefer J T, Patterson J W, Deacon D H et al. Dynamic changes in cellular infiltrates with repeated cutaneous vaccination: A histologic and immunophenotypic analysis. Journal of Translational Medicine 2010; 8:79.
12. Overwijk W, Hailemichael Y, Dai Z, Jaffarzad N, Hwu P. Peptide/incomplete Freund adjuvant emulsion depots are a graveyard for tumor antigen-specific CD8+ T cells Journal of Immunotherapy 2009; 32:971.
13. Kenter G G, Welters M J, Valentijn A R et al. Vaccination against HPV-16 oncoproteins for vulvar intraepithelial neoplasia. N Engl J Med 2009; 361:1838-1847.
14. Toes R E, Blom R J, Offringa R, Kast W M, Melief C J. Enhanced tumor outgrowth after peptide vaccination. Functional deletion of tumor-specific CTL induced by peptide vaccination can lead to the inability to reject tumors. J Immunol 1996; 156:3911-3918.
15. Toes R E, Offringa R, Blom R J, Melief C J, Kast W M. Peptide vaccination can lead to enhanced tumor growth through specific T-cell tolerance induction. Proc Natl Acad Sci USA 1996; 93:7855-7860.
16. Srinivasan M, Domanico S Z, Kaumaya P T, Pierce S K. Peptides of 23 residues or greater are required to stimulate a high affinity class II-restricted T cell response. Eur J Immunol 1993; 23:1011-1016.
17. Zwaveling S, Ferreira Mota S C, Nouta J et al. Established human papillomavirus type 16-expressing tumors are effectively eradicated following vaccination with long peptides. J Immunol 2002; 169:350-358.
18. Sercarz E E, Maverakis E. MHC-guided processing: binding of large antigen fragments. Nat Rev Immunol 2003; 3:621-629.
19. Bijker M S, van den Eeden S J, Franken K L, Melief C J, van der Burg S H, Offringa R. Superior induction of anti-tumor CTL immunity by extended peptide vaccines involves prolonged, D C-focused antigen presentation. Eur J Immunol 2008; 38:1033-1042.
20. Janssen E M, Droin N M, Lemmens E E et al. CD4+ T cell help helps control CD8+ T-cell memory via TRAIL-mediated activation-induced cell death. Nature 2010; 434:88-93.
21. van der Bruggen P, et al., Peptide Database, available at the Cancer Immunity website, 2011
22. Slingluff C L, Jr., Petroni G R, Chianese-Bullock K A et al. Immunologic and clinical outcomes of a randomized phase II trial of two multipeptide vaccines for melanoma in the adjuvant setting. Clin Cancer Res 2007; 13:6386-6395.
23. Thompson L W, Hogan K T, Caldwell J A et al. Preventing the spontaneous modification of an HLA-A2-restricted peptide at an N-terminal glutamine or an internal cysteine residue enhances peptide antigenicity. Journal of Immunotherapy 2004; 27:177-183.
24. Chianese-Bullock K A, Lewis S T, Sherman N E, Shannon J D, Slingluff C L, Jr. Multi-peptide vaccines vialed as peptide mixtures can be stable reagents for use in peptide-based immune therapies. Vaccine 2009; 27:1764-1770.
25. Kittlesen D J, Thompson L W, Gulden P H et al. Human melanoma patients recognize an HLA-A1-restricted CTL epitope from tyrosinase containing two cysteine residues: implications for tumor vaccine development [published erratum appears in J Immunol 1999 Mar. 1; 162(5):3106]. J I 1998; 160:2099-2106.
26. Sabbatini P, Tsuji T, Ferran L, Ritter E, Sedrak C, Tuballes K, Jungbluth A A, Ritter G, Aghajanian C, Bell-McGuinn K, Hensley M L, Konner J, Tew W, Spriggs D R, Hoffman E W, Venhaus R, Pan L, Salazar A M, Diefenbach C M, Old L J, Gnjatic S. Phase I trial of overlapping long peptides from a tumor self-antigen and poly-ICLC shows rapid induction of integrated immune response in ovarian cancer patients. et al., 2012, Clin. Cancer Res., 2012; 18:6497-6508.

27. Harris et al., The vaccine-site microenvironment induced by injection of incomplete Freund's adjuvant, with or without melanoma peptides. J Immunother. 2012 January; 35(1):78-88

28. Slingluff et al., Randomized multicenter trial of the effects of melanoma-associated helper peptides and cyclophosphamide on the immunogenicity of a multipeptide melanoma vaccine. J Clin Oncol. 2011 Jul. 20; 29(21):2924-32.

29. Schaefer et al., Dynamic changes in cellular infiltrates with repeated cutaneous vaccination: a histologic and immunophenotypic analysis. J Transl Med. 2010 Aug. 20; 8:79.

30. Slingluff C L et al., Immunogenicity for CD8+ and CD4+ T cells of 2 formulations of an incomplete freund's adjuvant for multipeptide melanoma vaccines. J Immunother. 2010 July-August; 33(6):630-8.

31. Slingluff et al., Effect of granulocyte/macrophage colony-stimulating factor on circulating CD8+ and CD4+ T-cell responses to a multipeptide melanoma vaccine: outcome of a multicenter randomized trial. Clin Cancer Res. 2009 Nov. 15; 15(22):7036-44.

32. Slingluff et al., Evaluation of the sentinel immunized node for immune monitoring of cancer vaccines. Ann Surg Oncol. 2008 December; 15(12):3538-49.

What is claimed is:

1. A composition comprising at least one isolated or synthetic peptide selected from the group consisting of peptides SEQ ID NOs: 1-8, optionally an adjuvant, and optionally a pharmaceutically acceptable carrier.

2. The composition of claim 1, said composition consisting of six peptides or seven peptides.

3. The composition of claim 2, wherein said composition consists of the six peptides having SEQ ID NOs:3-8 or the seven peptides SEQ ID NOs:2-8.

4. The composition of claim 1, further comprising at least one peptide selected from the group consisting of SEQ ID NOs:9-21.

5. The composition of claim 1, wherein the amount of each peptide per dose is from about 10 μg to about 10,000 μg.

6. The composition of claim 5, wherein the amount of each peptide per dose is from about 100 μg to about 1,000 μg.

7. The composition of claim 6, wherein the amount of each peptide per dose is 300 μg.

8. The composition of claim 1, wherein at least one of said peptides elicit an immunogenic response.

9. A method of eliciting an immunogenic response in a subject, said method comprising administering to said subject a composition comprising at least one isolated peptide selected from the group of peptides consisting of SEQ ID NOS: 1-8, optionally an adjuvant, and optionally a pharmaceutically acceptable carrier, whereby at least one of said peptides elicits an immunogenic response in said subject.

10. The method of claim 9, wherein at least one of said isolated peptides consisting of SEQ ID NOs:1, 2, 4-7, and 8 are administered to said subject.

11. The method of claim 9, wherein said composition comprises the six peptides consisting of SEQ ID NOs:3-8 or the seven peptides consisting of SEQ ID NOs:2-8.

12. A kit for eliciting an immunogenic response, said kit comprising at least one peptide selected from the group consisting of SEQ ID NOs:1-8 and optionally at least one isolated peptide selected from the group of peptides consisting of SEQ ID NOs: 9-21, optionally an adjuvant, and optionally a pharmaceutically acceptable carrier, an applicator, and an instructional material for the use thereof.

* * * * *

```
                    SEQUENCE LISTING

<160> NUMBER OF SEQ ID NOS: 21

<210> SEQ ID NO 1
<211> LENGTH: 30
<212> TYPE: PRT
<213> ORGANISM: homo sapiens

<400> SEQUENCE: 1

Phe Thr Ile Pro Tyr Trp Asp Trp Arg Asp Ala Glu Lys Ser Asp Ile
1               5                   10                  15

Cys Thr Asp Glu Tyr Met Gly Gly Gln His Pro Thr Asn Pro
            20                  25                  30

<210> SEQ ID NO 2
<211> LENGTH: 29
<212> TYPE: PRT
<213> ORGANISM: Homo sapiens

<400> SEQUENCE: 2

Ser Lys Ala Ser Ser Ser Leu Gln Leu Val Phe Gly Ile Glu Leu Met
1               5                   10                  15

Glu Val Asp Pro Ile Gly His Leu Tyr Ile Phe Ala Thr
            20                  25

<210> SEQ ID NO 3
<211> LENGTH: 30
<212> TYPE: PRT
<213> ORGANISM: Homo sapiens

<400> SEQUENCE: 3

Ser Met His Asn Ala Leu His Ile Tyr Met Asp Gly Thr Met Ser Gln
1               5                   10                  15

Val Gln Gly Ser Ala Asn Asp Pro Ile Phe Leu Leu His His
            20                  25                  30

<210> SEQ ID NO 4
<211> LENGTH: 30
<212> TYPE: PRT
<213> ORGANISM: Homo sapiens

<400> SEQUENCE: 4

Val Pro Leu Ala His Ser Ser Ser Ala Phe Thr Ile Met Asp Gln Val
1               5                   10                  15

Pro Phe Ser Val Ser Val Ser Gln Leu Arg Ala Leu Asp Gly
            20                  25                  30
```

-continued

```
<210> SEQ ID NO 5
<211> LENGTH: 30
<212> TYPE: PRT
<213> ORGANISM: Homo sapiens

<400> SEQUENCE: 5

Val Ile Trp Glu Ala Leu Asn Met Met Gly Leu Tyr Asp Gly Met Glu
1               5                   10                  15

His Leu Ile Tyr Gly Glu Pro Arg Lys Leu Leu Thr Gln Asp
            20                  25                  30

<210> SEQ ID NO 6
<211> LENGTH: 31
<212> TYPE: PRT
<213> ORGANISM: Homo Sapiens

<400> SEQUENCE: 6

Leu Leu His Leu Ala Val Ile Gly Ala Leu Ala Val Gly Ala Thr
1               5                   10                  15

Lys Val Pro Arg Asn Gln Asp Trp Leu Gly Val Ser Arg Gln Leu
            20                  25                  30

<210> SEQ ID NO 7
<211> LENGTH: 30
<212> TYPE: PRT
<213> ORGANISM: Homo sapiens

<400> SEQUENCE: 7

Ser Arg Glu Glu Glu Gly Pro Ser Thr Ser Cys Ile Leu Glu Ser Leu
1               5                   10                  15

Phe Arg Ala Val Ile Thr Lys Lys Val Ala Asp Leu Val Gly
            20                  25                  30

<210> SEQ ID NO 8
<211> LENGTH: 29
<212> TYPE: PRT
<213> ORGANISM: Homo sapiens

<400> SEQUENCE: 8

Phe Thr Ile Pro Tyr Trp Asp Trp Arg Asp Ala Glu Lys Ser Asp Ile
1               5                   10                  15

Cys Thr Asp Glu Tyr Met Gly Gly Gln His Pro Thr Asn
            20                  25

<210> SEQ ID NO 9
<211> LENGTH: 12
<212> TYPE: PRT
<213> ORGANISM: Homo sapiens

<400> SEQUENCE: 9

Asp Ala Glu Lys Ser Asp Ile Cys Thr Asp Glu Tyr
1               5                   10

<210> SEQ ID NO 10
<211> LENGTH: 9
<212> TYPE: PRT
<213> ORGANISM: Homo sapiens

<400> SEQUENCE: 10

Glu Val Asp Pro Ile Gly His Leu Tyr
1               5

<210> SEQ ID NO 11
```

```
<211> LENGTH: 9
<212> TYPE: PRT
<213> ORGANISM: Homo sapiens

<400> SEQUENCE: 11

Tyr Met Asp Gly Thr Met Ser Gln Val
1               5

<210> SEQ ID NO 12
<211> LENGTH: 9
<212> TYPE: PRT
<213> ORGANISM: Homo sapiens

<400> SEQUENCE: 12

Ile Met Asp Gln Val Pro Phe Ser Val
1               5

<210> SEQ ID NO 13
<211> LENGTH: 9
<212> TYPE: PRT
<213> ORGANISM: Homo sapiens

<400> SEQUENCE: 13

Gly Leu Tyr Asp Gly Met Glu His Leu
1               5

<210> SEQ ID NO 14
<211> LENGTH: 9
<212> TYPE: PRT
<213> ORGANISM: Homo sapiens

<400> SEQUENCE: 14

Ala Leu Leu Ala Val Gly Ala Thr Lys
1               5

<210> SEQ ID NO 15
<211> LENGTH: 9
<212> TYPE: PRT
<213> ORGANISM: Homo sapiens

<400> SEQUENCE: 15

Ser Leu Phe Arg Ala Val Ile Thr Lys
1               5

<210> SEQ ID NO 16
<211> LENGTH: 9
<212> TYPE: PRT
<213> ORGANISM: Homo sapiens

<400> SEQUENCE: 16

Met Pro Phe Ala Thr Pro Met Glu Ala
1               5

<210> SEQ ID NO 17
<211> LENGTH: 9
<212> TYPE: PRT
<213> ORGANISM: Homo sapiens

<400> SEQUENCE: 17

Leu Ala Met Pro Phe Ala Thr Pro Met
1               5

<210> SEQ ID NO 18
<211> LENGTH: 9
<212> TYPE: PRT
```

```
<213> ORGANISM: Homo sapiens

<400> SEQUENCE: 18

Ala Arg Gly Arg Glu Ser Arg Leu Leu
1               5

<210> SEQ ID NO 19
<211> LENGTH: 12
<212> TYPE: PRT
<213> ORGANISM: Homo sapiens

<400> SEQUENCE: 19

Glu Phe Tyr Leu Ala Met Pro Phe Ala Thr Pro Met
1               5                   10

<210> SEQ ID NO 20
<211> LENGTH: 13
<212> TYPE: PRT
<213> ORGANISM: Homo sapiens

<400> SEQUENCE: 20

Pro Phe Ala Thr Pro Met Glu Ala Glu Arg Ala Arg Arg
1               5                   10

<210> SEQ ID NO 21
<211> LENGTH: 14
<212> TYPE: PRT
<213> ORGANISM: Homo sapiens

<400> SEQUENCE: 21

Leu Leu Glu Phe Tyr Leu Ala Met Pro Phe Ala Thr Pro Met
1               5                   10
```